(12) United States Patent
Patel et al.

(10) Patent No.: US 8,682,445 B2
(45) Date of Patent: Mar. 25, 2014

(54) PATIENT MANAGEMENT SYSTEM FOR TREATING DEPRESSION USING AN IMPLANTABLE MEDICAL DEVICE

(75) Inventors: Sejal B. Patel, Pearland, TX (US); Jason D. Begnaud, Houston, TX (US); Chris G. DuPont, League City, TX (US); Albert A. Rodriguez, Friendswood, TX (US)

(73) Assignee: Cyberonics, Inc., Houston, TX (US)

( * ) Notice: Subject to any disclaimer, the term of this patent is extended or adjusted under 35 U.S.C. 154(b) by 99 days.

(21) Appl. No.: 11/495,471

(22) Filed: Jul. 28, 2006

(65) Prior Publication Data

US 2008/0027487 A1  Jan. 31, 2008

(51) Int. Cl.
*A61N 1/00* (2006.01)

(52) U.S. Cl.
USPC .......................................................... 607/60

(58) Field of Classification Search
USPC ................... 607/45, 59, 30; 600/300
See application file for complete search history.

(56) References Cited

U.S. PATENT DOCUMENTS

| | | | | |
|---|---|---|---|---|
| 6,066,163 A * | 5/2000 | John | ............................. | 607/45 |
| 6,366,813 B1 * | 4/2002 | DiLorenzo | ...................... | 607/45 |
| 6,425,764 B1 | 7/2002 | Lamson | ........................ | 434/236 |
| 6,463,328 B1 * | 10/2002 | John | ............................. | 607/45 |
| 6,873,872 B2 * | 3/2005 | Gluckman et al. | ................ | 607/2 |
| 7,076,307 B2 * | 7/2006 | Boveja et al. | .................... | 607/45 |
| 2004/0122484 A1 * | 6/2004 | Hatlestad et al. | ............... | 607/60 |
| 2004/0133080 A1 * | 7/2004 | Mazar et al. | .................... | 600/300 |
| 2004/0133248 A1 * | 7/2004 | Frei et al. | ........................ | 607/45 |
| 2004/0152946 A1 | 8/2004 | Franck | ............................ | 600/25 |
| 2004/0199217 A1 * | 10/2004 | Lee et al. | ........................ | 607/48 |
| 2004/0260356 A1 * | 12/2004 | Kara et al. | ....................... | 607/45 |
| 2005/0043774 A1 * | 2/2005 | Devlin et al. | .................... | 607/45 |
| 2005/0049651 A1 * | 3/2005 | Whitehurst et al. | ............ | 607/45 |
| 2005/0171088 A1 * | 8/2005 | Ault et al. | ................ | 514/211.13 |
| 2005/0182453 A1 * | 8/2005 | Whitehurst et al. | ............ | 607/45 |
| 2005/0282911 A1 * | 12/2005 | Hakkarainen et al. | ........ | 514/662 |
| 2006/0015153 A1 | 1/2006 | Gliner et al. | .................... | 607/45 |
| 2006/0149337 A1 | 7/2006 | John | .............................. | 607/45 |

OTHER PUBLICATIONS

MedeicineNet, Inc."Definition of Nerves, cranial", Web, Jan. 25, 2010. <http://www.medterms.com/script/main/art.asp?articlekey=7578>.*
UW Faculty Web Server. "Cranial Nerves", Last Web Update: Sep. 2, 2008. <http://faculty.washington.edu/chudler/cranial.html>.*
PCT/US2007/016315 Search Report (Dec. 7, 2007).

* cited by examiner

*Primary Examiner* — Allen Porter, Jr.
(74) *Attorney, Agent, or Firm* — Cyberonics, Inc.

(57) ABSTRACT

A method, system, graphical user interface, and apparatus are provided for performing a patient management function for treating depression using an implantable medical device. At least one patient parameter relating to an electrical signal provided by the implantable medical device for treating depression is acquired. At least one therapy parameter defining the electrical signal is correlated with at least one patient parameter. An indication relating to the correlation of the therapy parameter and the patient parameter is provided.

21 Claims, 12 Drawing Sheets

VNS Therapy ver. x.0

Model 102
S/N 1627  Pt. ID. ABC

| | | |
|---|---|---|
| Output Current (mA) | 1.00 | New |
| Signal Frequency (Hz) | 30 | New |
| Pulse Width (uSec) | 500 | New |
| Signal On Time (Sec) | 14 | New |
| Signal Off Time (min) | 5.0 | New |
| Mag. Current (mA) | 1.25 | New |
| Mag. On Time (Sec) | 60 | New |
| Mag. Pulse Wth (uSec) | 500 | New |

Near End of Service: NO

[Program]

VNS Therapy ver. x.0

PROGRAM PATIENT DATA

Patient ID Set To -- ABC
Implant Date Set To -- 01/11/01
Indication Set To -- Depression
Lead Model and S/N Set To -- 302-20/1627

Set Patient ID To  [ABC]
Set Implant Date To  [01/11/2004]
Set Indication To  [Depression]
Set Lead Model & S/N To  [302-20] [1152]

[Program]  [Cancel]

```
123 1 2 3 4 5 6 7 8 9 0 - = 
Tab  q w e r t y u i o p [ ] 
Cap  a s d f g h j k l ; ' 
Shift  z x c v b n m , . / 
Ctl  alt  ` Space
```

| VNS Therapy ver. x.0 ▼ 10:54 |
|---|

Patient Management Screen

Patient ID: ABC    Visit Date 01/11/03

|   | Name | Dose |   |
|---|---|---|---|
| Med 1: | Prozac ▼ | 100 mg ▼ | tid ▼ |
| Med 2: | Effexor ▼ | 50 mg ▼ | bid ▼ |
| Med 3: | None ▼ | 00 mg ▼ | N/A ▼ |
| Med 4: | None ▼ | 00 mg ▼ | N/A ▼ |

[View Graph]    [Save]    [Cancel]

```
123 1 2 3 4 5 6 7 8 9 0 - =    ↓
Tab q w e r t y u i o p [ ]    ↵
Cap a s d f g h j k l ; "      ←
Shift z x c v b n m , . /      ↑ →
Ctl  au \          Space           ▯
```

| VNS Therapy ver. x.0 ▼ 10:54 |
|---|

Patient Management

Patient ID: ABC    Visit Date 01/11/03

Quality of Life  [Generic Scale ▼]

1-Very Poor   3-Average   5-Excellent
2-Poor        4-Good

| Alertness | 5 - Excellent ▼ |
| Verbal Skills | 4 - Good ▼ |
| Mood | N/A ▼ |
| Achievements | N/A ▼ |
| Memory | N/A ▼ |
| Overall QOL | N/A ▼ |

Total QOL Score = N/A

[Enter Medications]    [View Graph]
[Save]                 [Cancel]

VNS Therapy ver. x.0 ▼ 10:54

Patient Management Screen

Patient ID: ABC    Visit Date 01/11/03

| | Name | | Dose | |
|---|---|---|---|---|
| Med 1: | Abilify ▼ | 75 mg ▼ | tid ▼ |
| Med 2: | Risperdal ▼ | 25 mg ▼ | bid ▼ |
| Med 3: | None | 00 mg ▼ | N/A ▼ |
| Med 4: | None | 00 mg ▼ | N/A ▼ |

[View Graph]  [Save]  [Cancel]

```
123 1 2 3 4 5 6 7 8 9 0 - = ↓
Tab  q w e r t y u i o p [ ] "
Cap  a s d f g h j k l ; ' ↵
Shift z x c v b n m , . / ↑
Ctl  au '        Space      ← ↓ →
```

FIG. 12

VNS Therapy ver. x.0 ▼ 10:54

Patient Management

Patient ID: ABC    Visit Date 01/11/03

Graphing Options:

● HRDS Score and IDSSR Score
● Change (Output * Pulse Width)
○ Output Current
○ Signal Frequency
○ Pulse Width
○ Duty Cycle ● Quality of Life
● Change (Output * Pulse Width)
● Output Current
● Signal Frequency
● Pulse Width
● Duty Cycle

[Launch Graph]        [Cancel]

PATIENT MANAGEMENT SYSTEM FOR TREATING DEPRESSION USING AN IMPLANTABLE MEDICAL DEVICE

BACKGROUND OF THE INVENTION

1. Field of the Invention

This invention relates generally to implantable medical device systems, and, more particularly, a patient management system to provide an interactive forum for managing patient care for treating depression using an implantable medical device (IMD).

2. Description of the Related Art

Many advancements have been made in treating diseases such as depression and epilepsy. Therapies using electrical signals for treating these diseases have been found to effective. Implantable medical devices have been effectively used to deliver therapeutic stimulation to various portions of the human body (e.g., the vagus nerve) for treating these diseases. As used herein, "stimulation" or "stimulation signal" refers to the application of an electrical, mechanical, magnetic, electro-magnetic, photonic, audio and/or chemical signal to a neural structure in the patient's body. The signal is an exogenous signal that is distinct from the endogenous electrical, mechanical, and chemical activity (e.g., afferent and/or efferent electrical action potentials) generated by the patient's body and environment. In other words, the stimulation signal (whether electrical, mechanical, magnetic, electro-magnetic, photonic, audio or chemical in nature) applied to the nerve in the present invention is a signal applied from an artificial source, e.g., a neurostimulator.

A "therapeutic signal" refers to a stimulation signal delivered to a patient's body with the intent of treating a disorder by providing a modulating effect to neural tissue. The effect of a stimulation signal on neuronal activity is termed "modulation"; however, for simplicity, the terms "stimulating" and "modulating", and variants thereof, are sometimes used interchangeably herein. In general, however, the delivery of an exogenous signal itself refers to "stimulation" of the neural structure, while the effects of that signal, if any, on the electrical activity of the neural structure are properly referred to as "modulation." The modulating effect of the stimulation signal upon the neural tissue may be excitatory or inhibitory, and may potentiate acute and/or long-term changes in neuronal activity. For example, the "modulating" effect of the stimulation signal to the neural tissue may comprise one more of the following effects: (a) initiation of an action potential (afferent and/or efferent action potentials); (b) inhibition or blocking conduction of action potentials, whether endogenous or exogenously induced, including hyperpolarizing and/or collision blocking, (c) affecting changes in neurotransmitter/neuromodulator release or uptake, and (d) changes in neuro-plasticity or neurogenesis of brain tissue.

Electrical neurostimulation may be provided by implanting an electrical device underneath the skin of a patient and delivering an electrical signal to a nerve such as a cranial nerve. In one embodiment, the electrical neurostimulation involves sensing or detecting a body parameter, with the electrical signal being delivered in response to the sensed body parameter. This type of stimulation is generally referred to as "active," "feedback," or "triggered" stimulation. In another embodiment, the system may operate without sensing or detecting a body parameter once the patient has been diagnosed with a medical condition that may be treated by neurostimulation. In this case, the system may apply a series of electrical pulses to the nerve (e.g., a cranial nerve such as a vagus nerve) periodically, intermittently, or continuously throughout the day, or over another predetermined time interval. This type of stimulation is generally referred to as "passive," "non-feedback," or "prophylactic," stimulation. The stimulation may be applied by an implantable medical device that is implanted within the patient's body. In another alternative embodiment, the signal may be generated by an external pulse generator outside the patient's body, coupled by an RF or wireless link to an implanted electrode.

Generally, neurostimulation signals that perform neuromodulation are delivered by the implantable device via one or more leads. The leads generally terminate into electrodes, which are affixed onto a tissue in the patient's body. For example, a number of electrodes may be attached to various points of a nerve or other tissue inside a human body for delivery of neurostimulation.

State-of-the-art implantable medical systems utilize an external device to communicate with the IMD for programming the therapeutical electrical signal to be delivered by the implanted device, performing diagnostics, and making adjustments to one or more parameters of defining the therapeutic electrical signal. A physician may investigate the progress of a particular therapy regimen given to a patient during office visits. The physician may examine the patient and make a determination as to the efficacy of the therapy being delivered, and may use the external device to reprogram or adjust various stimulation parameters that will modify subsequent therapy delivered to the patient.

Among the problems associated with state-of-the-art implanted neurostimulators includes the fact that tedious record-keeping and study of charts are required to perform therapy management. When the physician evaluates a patient, various settings for therapy delivered by the IMD are documented in the patient's chart at each visit. At subsequent visits, the physician may then examine previous entries into the chart (e.g., the physician may study the various parameters defining the therapeutic electrical signal, medications taken by the patient, etc.) to make adjustments to the therapy delivered by the IMD.

The process of documenting the changes in the parameters, medication and patient evaluation may become quite tedious, with a corresponding risk that important information may not be collected or may not be incorporated into the adjustments made to the therapy to improve or maintain efficacy. Further, examining all of the previous chart entries along with the current patient evaluation to determine an appropriate therapy for the patient may become cumbersome. Further, inherent changes or other trends may not be easily detected by the physician upon a review of the various entries in the patient's chart. Therefore, opportunities to improve the efficacy of the therapy may be inadvertently missed due to the tedious nature of patient evaluation and the voluminous data entries made to a patient's chart, as well as to insufficient or improper evaluation of the data collected.

The present invention is directed to overcoming, or at least reducing, the effects of one or more of the problems set forth above.

SUMMARY OF THE INVENTION

In one aspect, the present invention provides for performing a patient management function for treating depression using an implantable medical device. At least one patient parameter relating to an electrical signal provided by the implantable medical device for treating depression is acquired. At least one therapy parameter defining the electrical signal is correlated with the at least one patient parameter.

An indication relating to the correlation of the therapy parameter and the patient parameter is provided.

In another aspect, a graphical user interface is provided for performing a patient management function for treating depression using an implantable medical device. The graphical user interface of the present invention includes a display region. The display region is adapted to display a visual indication of a correlation between at least one patient parameter relating to an electrical signal provided by the implantable medical device for treating depression and at least one therapy parameter defining the electrical signal delivered by the implantable medical device.

In yet another aspect of the present invention, a computer readable program storage device encoded with instructions is provided for performing a patient management function for treating depression using an implantable medical device. The computer readable program storage device is encoded with instructions that, when executed by a computer, performs a method, which comprises: acquiring at least one patient parameter relating to an electrical signal provided by the implantable medical device for treating depression; and correlating at least one therapy parameter defining the electrical signal with the at least one patient parameter.

BRIEF DESCRIPTION OF THE DRAWINGS

The invention may be understood by reference to the following description taken in conjunction with the accompanying drawings, in which like reference numerals identify like elements, and in which:

FIG. 5 illustrates a GUI screen that provides various information relating to an IMD implanted in a particular patient, wherein the GUI screen may provide for interactive inputs, according to some embodiments of the present disclosure;

FIG. 6 illustrates another exemplary screen that may be driven by a patient management unit and displayed by a GUI interface unit, according to some embodiments of the present disclosure;

FIG. 7 illustrates a screen driven by a patient management unit and displayed on a GUI interface unit that provides data indicative of a list of patient visits, according to some embodiments of the present disclosure;

FIG. 8 illustrates a screen driven by a patient management unit displayed by a GUI interface unit to allow input of a depression score on one or more depression scoring systems, according to some embodiments of the present disclosure;

FIG. 9 illustrates another screen driven by the patient management unit and displayed by the GUI interface unit 240 relating to a plurality of quality of life factors, according to some embodiments of the present disclosure;

FIG. 10 illustrates an input screen provided to allow a healthcare provider or patient to enter various medications currently being prescribed to a patient, according to some embodiments of the present disclosure;

FIG. 11 illustrates an interface screen that includes various augmenting agents and/or dosages that the patient may have been prescribed, according to some embodiments of the present disclosure;

FIG. 12 illustrates an interface screen that provides display options for a user for viewing various correlations of data in a graphical form, according to some embodiments of the present disclosure;

DETAILED DESCRIPTION OF SPECIFIC EMBODIMENTS

Figure 1:
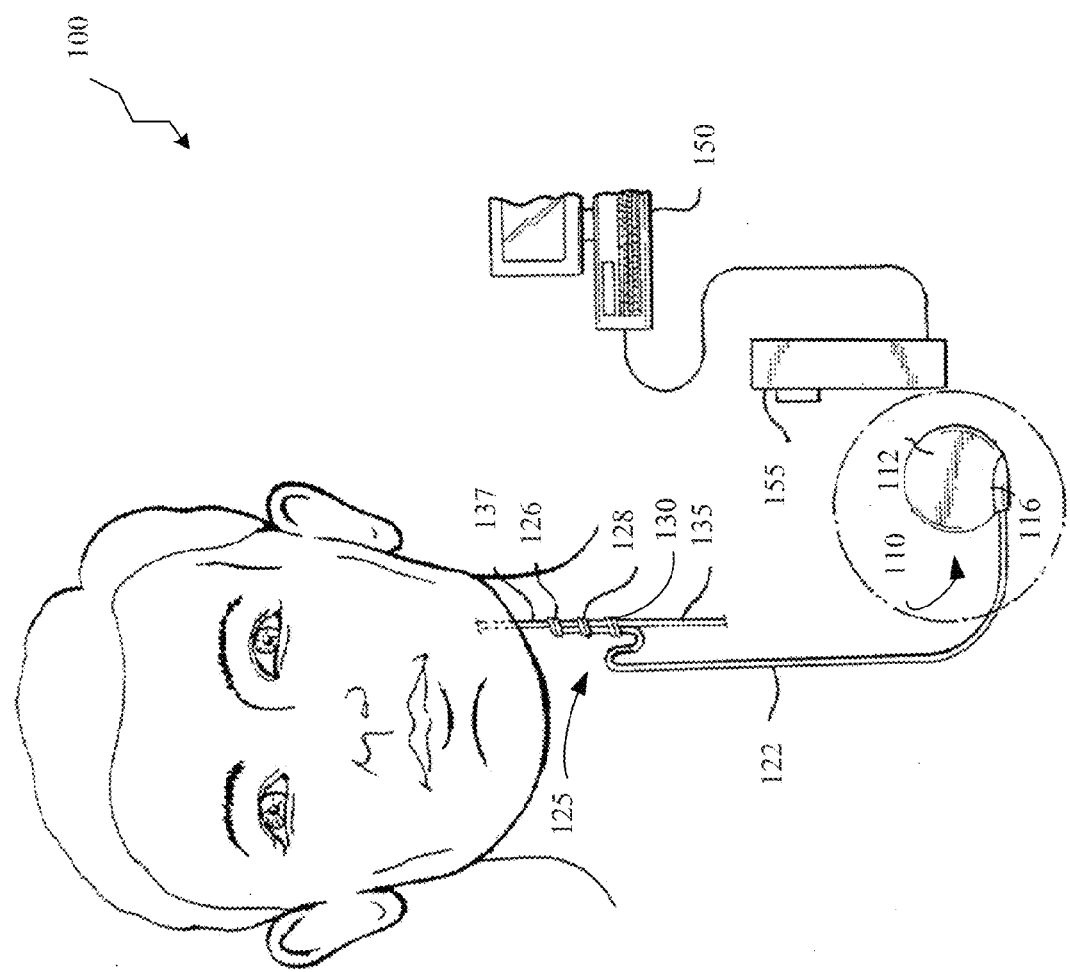
FIG. 1 provides a stylized diagram of an implantable medical device implanted into a patient's body for providing an electrical signal to a portion of the patient's body for treating depression, in accordance with one illustrative embodiment of the present invention.

Illustrative embodiments of the invention are described herein. In the interest of clarity, not all features of an actual implementation are described in this specification. In the development of any such actual embodiment, numerous implementation-specific decisions must be made to achieve the design-specific goals, which will vary from one implementation to another. It will be appreciated that such a development effort, while possibly complex and time-consuming, would nevertheless be a routine undertaking for persons of ordinary skill in the art having the benefit of this disclosure.

This document does not intend to distinguish between components that differ in name but not function. In the following discussion and in the claims, the terms "including" and "includes" are used in an open-ended fashion, and thus should be interpreted to mean "including, but not limited to." Also, the term "couple" or "couples" is intended to mean either a direct or an indirect electrical connection. "Direct contact," "direct attachment," or providing a "direct coupling" indicates that a surface of a first element contacts the surface of a second element with no substantial attenuating medium therebetween. The presence of substances, such as bodily fluids, that do not substantially attenuate electrical connections does not vitiate direct contact. The word "or" is used in the inclusive sense (i.e., "and/or") unless a specific use to the contrary is explicitly stated.

The term "electrode" or "electrodes" described herein may refer to one or more stimulation electrodes (i.e., electrodes for delivering an electrical signal generated by an IMD to a tissue), sensing electrodes (i.e., electrodes for sensing a physiological indication of a patient's body), and/or electrodes that are capable of delivering a stimulation signal as well as performing a sensing function.

Cranial nerve stimulation has been proposed to treat a number of nervous system disorders, including epilepsy and other movement disorders, depression, anxiety disorders and other neuropsychiatric disorders, dementia, head trauma, coma, migraine headache, obesity, eating disorders, sleep disorders, cardiac disorders (such as congestive heart failure and atrial fibrillation), hypertension, endocrine disorders (such as diabetes and hypoglycemia), and pain, among others. See, e.g., U.S. Pat. Nos. 4,867,164; 5,299,569; 5,269,303; 5,571,150; 5,215,086; 5,188,104; 5,263,480; 6,587,719; 6,609,025; 5,335,657; 6,622,041; 5,916,239; 5,707,400; 5,231,988; and 5,330,515. Despite the numerous proposed disorders for which cranial nerve stimulation has been proposed or suggested as a treatment option, the fact that detailed neural pathways for many (if not all) cranial nerves remain relatively unknown makes predictions of efficacy for any given disorder difficult. Even if such pathways were known, moreover, the precise stimulation parameters that would modulate particular pathways relevant to a particular disorder likewise are difficult to predict.

Despite the difficulties of predicting efficacy for particular disorders, the use of vagus nerve stimulation as a therapy for treatment-resistant depression has recently been approved as a therapy option. Although many patients respond well to the therapy, a significant number of patients must have the therapeutic electrical signal adjusted periodically to cause and/or maintain a positive therapeutic response. The present invention provides a patient management system for capturing, and incorporating into therapy decision-making process, information relevant to the patient's condition and course of treatment. More particularly, embodiments of the present invention provide for a patient management system for automatic documentation and evaluation of various patient parameters and therapy parameters relating to an operation of an IMD system for treating depression. The patient management system provided by embodiments of the present invention facilitates the processes of documentation and analysis of various patient and stimulation parameters associated with depression. This documentation process may be useful in determining various trends relating to treatment efficacy. Using this data, a physician may determine whether changes in therapy and/or medication would be desirable.

The patient management system of the present invention provides for a software module that is capable of acquiring, storing, and processing various forms of data, e.g., patient data/parameters (e.g., physiological data, side-effect data such as effects on heart rate and breathing, brain-activity parameter, disease progression or regression data, self-evaluation data, depression score/ratings data, quality of life data, etc.), therapy parameter data, etc. Therapy parameters may include, but are not limited to, electrical signal parameters relating to the therapeutic signals delivered by the IMD, medication parameters (e.g., dosages, frequency of medication provided to the patient, etc), and/or any other therapeutic treatment parameter. In an alternative embodiment, the term "therapy parameters" refers to electrical signal parameters relating to the therapeutic signals delivered by the IMD. Other diagnostics and physician interaction data may also be stored by the patient management system of the present invention. For example, the patient management system may provide for storage of the date of a patient's visit, changes made to various parameters associated with the IMD, physician input, patient input, etc.

In one embodiment, the patient management system of the present invention also provides for a graphic user interface (GUI) that may be interactive. The GUI of the patient management system may facilitate the entry of various physician inputs, such as the selection of a mode of operation for the patient management system. Once a certain mode, such as an input mode, evaluation mode, therapy adjustment mode, etc., is initiated by a user (e.g., a physician, a nurse, or a medical technician) the patient management tool may provide for an interactive interface to acquire, process, store and/or display various data associated with a therapy delivered to a patient. For example, a physician can enter information such as a patient's depression score, a "quality of life" input factor, patient's medication during each visit, etc. The patient management system may then store this information and provide a trend-type information display using the GUI. For example, by analyzing the information relating to various depression scores, quality of life input, etc., along with therapy parameters over time, the physician may then evaluate the progress of therapy and make appropriate adjustments. Various therapy settings, medication levels, etc., may be adjusted to improve the patient's efficacy and quality of life.

Although not so limited, a system capable of implementing embodiments of the present invention is described below. FIG. 1 depicts a stylized implantable medical system 100 for implementing one or more embodiments of the present invention. An electrical signal generator 110 is provided, having main body 112 comprising a case or shell with a header 116 (FIG. 1) for connecting to a lead 122. The generator 110 is implanted in the patient's chest in a pocket or cavity formed by the implanting surgeon just below the skin (indicated by a dotted line 145), similar to the implantation procedure for a pacemaker pulse generator.

A nerve electrode assembly 125, preferably comprising a plurality of electrodes having at least an electrode pair, is conductively connected to the distal end of an insulated, electrically conductive lead assembly 122, which preferably comprises a plurality of lead wires (one wire for each electrode). Each electrode in the electrode assembly 125 may operate independently or alternatively, may operate in conjunction with each other.

Lead assembly 122 is attached at its proximal end to connectors on the header 116 of generator 110. The electrode assembly 125 may be surgically coupled to a vagus nerve 127 in the patient's neck or at another location, e.g., near the patient's diaphragm. Other cranial nerves may also be used to deliver the electrical signal. In one embodiment, the electrode assembly 125 comprises a bipolar stimulating electrode pair 126, 128. Suitable electrode assemblies are available from Cyberonics, Inc., Houston, Tex., USA as the Model 302 electrode assembly. However, persons of skill in the art will appreciate that many electrode designs could be used in the present invention. In one embodiment, the two electrodes are wrapped about the vagus nerve, and the electrode assembly 125 may be secured to the nerve 127 by a spiral anchoring tether 130 such as that disclosed in U.S. Pat. No. 4,979,511 issued Dec. 25, 1990 to Reese S. Terry, Jr. and assigned to the same assignee as the instant application. Lead assembly 122 is secured, while retaining the ability to flex with movement of the chest and neck, by a suture connection 130 to nearby tissue (not shown).

In alternative embodiments, the electrode assembly 125 may comprise temperature sensing elements and/or heart rate sensor elements. Other sensors may also be employed to trigger active stimulation. Both passive and active stimulation may be combined or delivered by a single IMD according to the present invention. Either or both modes may be appropriate to treat a specific patient under observation.

The electrical pulse generator 110 may be programmed with an external computer 150 using programming software based on the description herein. A programming wand 155 may be used to facilitate radio frequency (RF) communication between the computer 150 and the pulse generator 110.

The programming wand 155 and computer 150 permit noninvasive communication with the generator 110 after the latter is implanted.

Figure 2A:
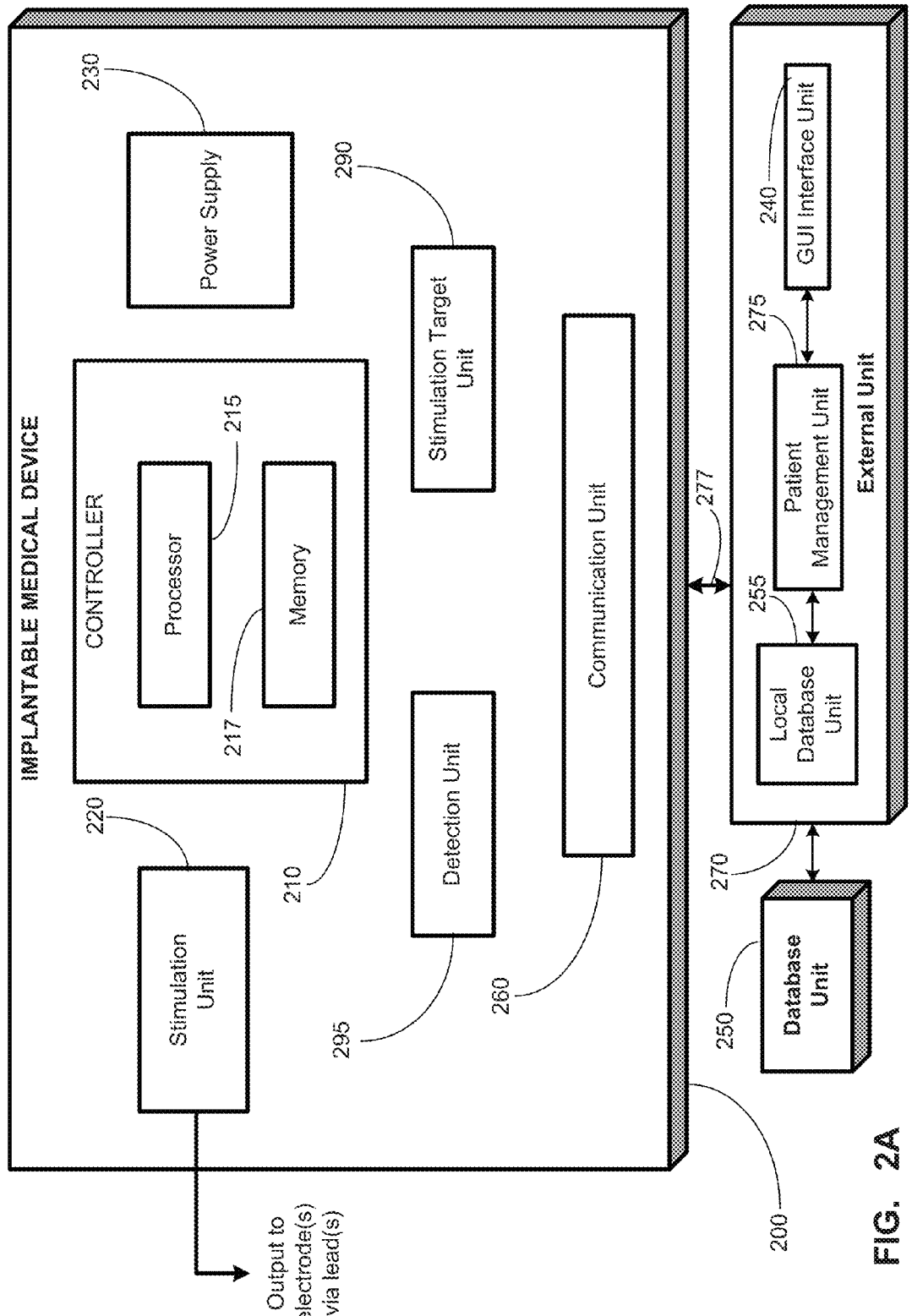
FIG. 2A is a block diagram of an implantable medical system that includes an implantable medical device and an external device, and a graphical user interface unit for providing a patient management system, in accordance with one illustrative embodiment of the present invention.

Turning now to FIG. 2A, a block diagram depiction of the IMD 200 is provided, in accordance with an illustrative embodiment of the present invention. The IMD 200 (such as generator 110 from FIG. 1) may comprise a controller 210 capable of controlling various aspects of the operation of the IMD 200. The controller 210 is capable of receiving internal data or external data and generating and delivering an electrical signal to target tissues of the patient's body. For example, the controller 210 may receive manual instructions from an operator externally, or may generate the electrical signal based on internal calculations and programming. The controller 210 is capable of affecting substantially all functions of the IMD 200.

The controller 210 may comprise various components, such as a processor 215, a memory 217, etc. The processor 215 may comprise one or more microcontrollers, microprocessors, etc., capable of performing various executions of software components. The memory 217 may comprise various memory portions where a number of types of data (e.g., internal data, external data instructions, software codes, status data, diagnostic data, etc.) may be stored. The memory 217 may comprise random access memory (RAM) dynamic random access memory (DRAM), electrically erasable programmable read-only memory (EEPROM), flash memory, etc.

The IMD 200 may also comprise a stimulation unit 220 capable of generating and delivering electrical signals to one or more electrodes via leads. A lead assembly 122 may be coupled to the IMD 200. Therapy may be delivered to the leads comprising the lead assembly 122 by the stimulation unit 220 based upon instructions from the controller 210. The stimulation unit 220 may comprise various circuitry, such as stimulation signal generators, impedance control circuitry to control the impedance "seen" by the leads, and other circuitry that receives instructions relating to the delivery of the electrical signal to tissue. The stimulation unit 220 is capable of delivering a controlled current stimulation signal over the leads 122.

The IMD 200 may also comprise a power supply 230. The power supply 230 may comprise a battery, voltage regulators, capacitors, etc., to provide power for the operation of the IMD 200, including delivering the therapeutic electrical signal. The power supply 230 comprises a power source that in some embodiments may be rechargeable. In other embodiments, a non-rechargeable power source may be used. The power supply 230 provides power for the operation of the IMD 200, including electronic operations and the electrical signal generation and delivery functions. The power supply 230 may comprise a lithium/thionyl chloride cell or a lithium/carbon monofluoride cell. Other battery types known in the art of implantable medical devices may also be used.

The IMD 200 may also comprise a communication unit 260 capable of facilitating communications between the IMD 200 and various devices. In particular, the communication unit 260 is capable of providing transmission and reception of electronic signals to and from an external unit 270, such as computer 150 and wand 155 (FIG. 1). The communication unit 260 may be hardware, software, firmware, or any combination thereof.

The external unit 270 may be a device that is capable of programming various modules and electrical signal parameters of the IMD 200. In one embodiment, the external unit 270 is a computer system capable of executing a data-acquisition program. The external unit 270 may be controlled by a healthcare provider, such as a physician, at a base station in, for example, a doctor's office. In alternative embodiments, the external unit 270 may be controlled by a patient in a system providing less control over the operation of the IMD 200 than another external unit 270 controlled by a healthcare provider. Whether controlled by the patient or by a healthcare provider, the external unit 270 may be a computer, preferably a handheld computer or PDA, but may alternatively comprise any other device that is capable of electronic communications and programming. The external unit 270 may download various parameters and program software into the IMD 200 for programming the operation of the IMD, and may also receive and upload various status conditions and other data from the IMD 200. Communications between the external unit 270 and the communication unit 260 in the IMD 200 may occur via a wireless or other type of communication, represented generally by line 277 in FIG. 2A and FIG. 2B. This may occur using, e.g., wand 155 (FIG. 1) to communicate by RF energy with a generator 110.

The IMD 200 also comprises a detection unit 295 that is capable of detecting various patient parameters. For example, the detection unit 295 may comprise hardware, software, or firmware that are capable of determining data relating to one or more body parameters of the patient relevant to depression. Based upon the data deciphered by the detection unit 295, the IMD 200 may deliver the electrical signal to a portion of the vagus nerve to treat depression. In one embodiment, the detection unit 295 may be capable of detecting a feedback response from the patient. The feedback response may include a magnetic signal input, a tap input, a wireless data input to the IMD 200, etc. The feedback may be indicative of a pain and/or noxious threshold, wherein the threshold may be the limit of tolerance of discomfort for a particular patient.

The IMD 200 may also comprise an electrode selection unit 290 that is capable of directing an electrical signal to one or more electrodes that is operationally coupled to various portions of the vagus nerve. The stimulation target unit 290 may direct a stimulation signal to the left vagus main trunk, the right vagus main trunk, or a branch of the left or right vagus nerves, or may "steer" the electrical signal to particular nerve axons within the main vagus nerve trunk. In this way, the stimulation target unit is capable of targeting a predetermined portion of the vagus nerve. Therefore, based upon a particular type of data detected by the detection unit 295, the electrode selection unit 290 may provide a signal capable of generating afferent action potentials, efferent action potentials, blocking afferent and/or efferent action potentials, or a combination of the foregoing effects to treat depression.

The external unit 270 may comprise a patient management unit 275 that is capable of performing the various patient management processes described herein. The patient management unit 270 is capable of performing various diagnostics of the IMD 200, as well as acquiring, storing and/or processing data relating to the therapy delivered by the IMD 200. More detailed description of the patient management unit 270 is provided in FIG. 4 and accompanying description below.

In one embodiment, external unit 270 comprises a graphical user interface (GUI) interface unit 240, such as a graphical user interface (GUI) unit. It will be appreciated that GUI interface unit 240 may also be a separate unit from external unit 270. Regardless of whether the GUI interface unit 240 is part of, or separate from, external unit 270, the external unit is capable of driving various displays on the GUI interface unit 240. In one embodiment, the interface unit 240 is capable not only of receiving data from the external unit 270 for driving one or more displays, but also of receiving inputs from a user, such as a physician or patient, and transmitting the data to the patient management unit 275. The GUI interface unit 240 may be comprised of a variety of devices, including, but not limited to, a computer terminal, a cathode ray tube (CRT) device, a liquid crystal device (LCD) module, a plasma-display device, etc. The GUI interface unit 240 may be a touch sensitive screen monitor that is capable of detecting an external input from the user. It may also be a handheld device, such as a personal digital assistant (PDA), a pen input device, a portable computer device, etc.

In one embodiment, the external unit 270 may comprise a local database unit 255 from which the patient management unit 275 may receive data. Optionally or alternatively, the external unit 270 may also be coupled to a database unit 250, which may be separate from external unit 270 (e.g., a centralized database wirelessly linked to a handheld external unit 270). The database unit 250 and/or the local database unit 255 are capable of storing various patient data. This data may comprise patient parameter data acquired from a patient's body and/or therapy parameter data. The database unit 250 and/or the local database unit 255 may comprise data for a plurality of patients, and may be organized and stored in a variety of manners, such as in date format, severity of disease format, etc. The database unit 250 and/or the local database unit 255 may be relational databases in one embodiment. A physician may perform various patient management functions described below using the GUI interface unit 240, which may display data from the IMD 200 and/or data from the database unit 250 and/or the local database unit 255. Inputs into the GUI interface unit 240 may be sent to the IMD 200 to modify various parameters for stimulation.

One or more of the blocks illustrated in the block diagram of IMD 200, in FIG. 2A, may comprise hardware units, software units, firmware units or any combination thereof. Additionally, one or more blocks illustrated in FIG. 2A may be combined with other blocks, which may represent circuit hardware units, software algorithms, etc. Additionally, any number of the circuitry or software units associated with the various blocks illustrated in FIG. 2A may be combined into a programmable device, such as a field programmable gate array, an ASIC device, etc.

Figure 2B:
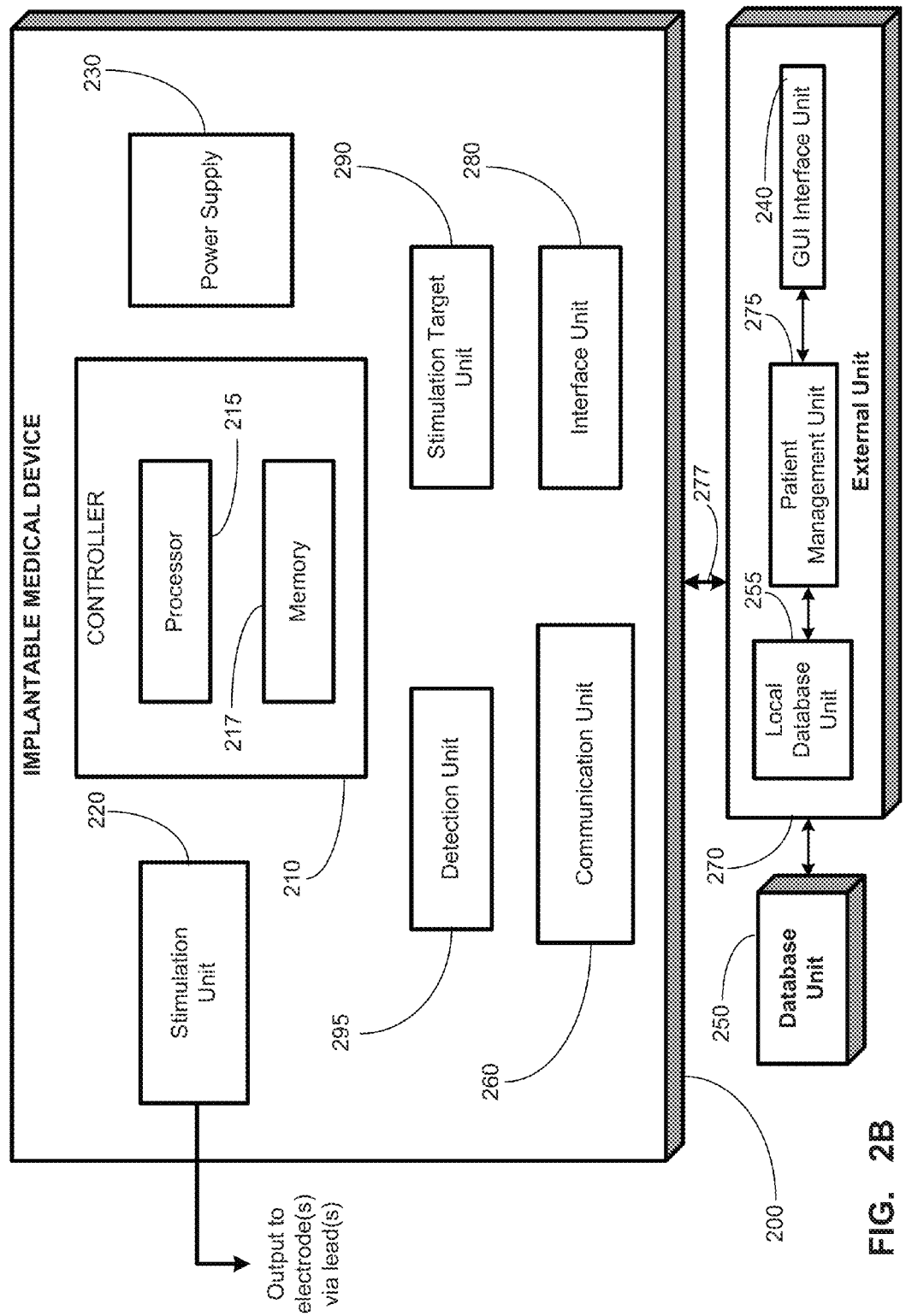
FIG. 2B is a block diagram of an implantable medical system that includes an implantable medical device and an external device, and a graphical user interface unit for providing a patient management system, in accordance with an alternative illustrative embodiment of the present invention.

Turning now to FIG. 2B, a block diagram depiction of the IMD 200 is provided, in accordance with an alternative illustrative embodiment of the present invention. The various blocks of FIG. 2B that correspond to similar blocks of FIG. 2A operate in a similar fashion. Additionally, the alternative embodiment of FIG. 2B also comprises an interface unit 280. The interface unit 280 that is capable of communications with the external unit 270. The interface unit 280 may receive instructions and/or data from the external unit 270 via the communication unit 260. The interface unit 280 is capable of various tasks, such as accessing the memory 217 in the IMD 200. Further, the interface unit 280 is capable of providing requested data to the external unit 270 to be displayed by the external unit 270. More detailed description of the interface unit 280 is provided in FIG. 3 and accompanying description below.

Figure 3:
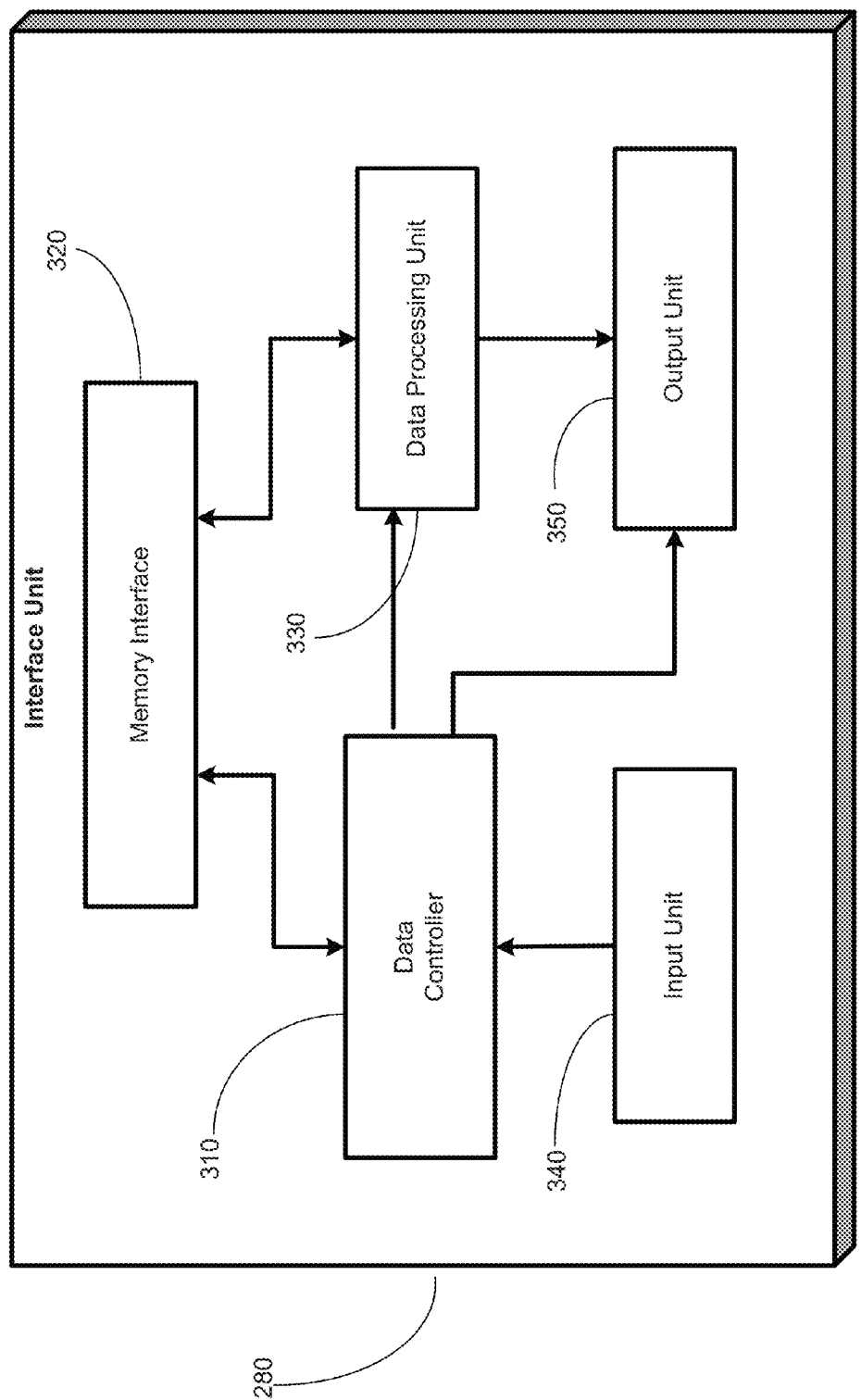
FIG. 3 is a more detailed block diagram of a graphical user interface unit of FIG. 2A or FIG. 2B, in accordance with one illustrative embodiment of the present invention.

Turning now to FIG. 3, a more detailed block diagram depiction of the interface unit 280 of FIG. 2B, in accordance with one illustrative embodiment of the present invention, is provided. The interface unit 280 may comprise a memory interface 320 that is capable of receiving data from, and/or storing data into the memory 217 of the IMD 200. The memory interface 320 may comprise various hardware and/or firmware objects to facilitate access to the memory 217.

The GUI interface 280 also comprises a Data controller 310. The Data controller 310 is capable of controlling the various functions performed by the interface unit 280, such as receiving and processing information from the external unit 270, as well as providing various parametric data to various portions of the IMD 200. The interface unit 280 may also comprise a data processing unit 330. The data processing unit 330 is capable of processing various patient parameter data and stimulation-related data. For example, upon a command from the external unit 270, the data processing unit 330 may process and correlate patient data with certain stimulation parameters that were used within a pre-determined time period in which the patient data was acquired. For example, after the delivery of a particular therapeutic stimulation cycle, within a predetermined time period, various patient parameters may be collected by the IMD 200. This data may then be correlated and organized in such a fashion that trends relating to the patient data in relationship to various stimulation parameters may be determined. Statistical and/or other types of data manipulation may also be performed by the data processing unit 330.

Further, the interface unit 280 may also comprise an input unit 340, which is capable of receiving data from the external unit 270 via the communication unit 360. Further, the GUI interface unit 340 may also comprise an output unit 350, which is capable of driving data from the interface unit 280 to the external unit 270. The input unit 340 may comprise various registers, buffers and/or amplifiers to process and streamline data, e.g., convert data from serial to parallel, or vice versa. The output unit 350 is also capable of registering, buffering and/or amplifying data for transmission from the interface unit 280 to the external unit 270. The interface unit 280 is capable of receiving instructions and providing for various responsive actions in the IMD 200, as well as collecting, processing, and/or storing data. The interface unit 280 provides for the ability for using a graphical user interface to provide interactivity between an external user e.g., a physician, and the IMD 200.

Figure 4:
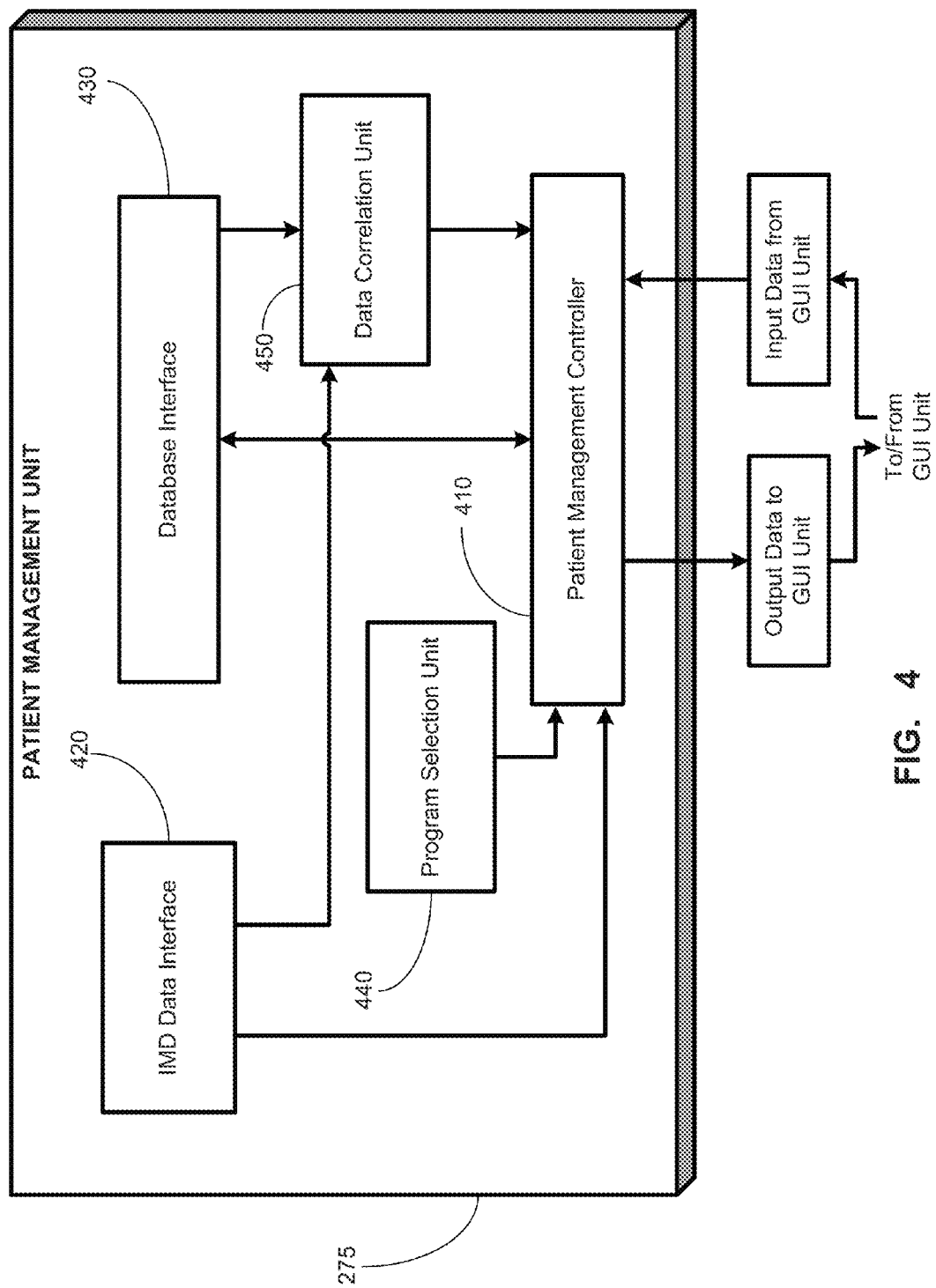
FIG. 4 is a more detailed block diagram depiction of a patient management unit of FIG. 2A or FIG. 2B, in accordance with one illustrative embodiment of the present invention.

FIG. 4 illustrates a more detailed block diagram depiction of the patient management unit 275 (FIG. 2), in accordance with one illustrative embodiment of the present invention. The patient management unit 275 may include a patient management controller 410 that is capable of performing the various patient management tasks described herein. The patient management controller 410 may be a microprocessor, a firmware object (e.g., a field programmable gate array (FPGA) or an ASIC device), and/or a software module. The patient management controller 410 is capable of extracting data from the database unit 250 (FIG. 2A and FIG. 2B) via a database interface 430. The database interface 430 may contain various amplifiers, buffers, registers and/or software modules to retrieve data from the database unit 250 or send data to the database unit 250. The patient management unit 275 may also comprise an IMD data interface 420 that is capable of receiving from or sending data to the IMD 200. The IMD data interface 420 may comprise various amplifiers, buffers, registers and/or software modules to send data to the IMD 200 and/or receive data from the IMD 200.

The patient management unit 275 may also comprise a program selection unit 440 that may be used to select the type of software program/code to be run by the external unit 270. The program selection unit 440 identifies to the external unit 270 the type of IMD 200 that is being accessed. For example, the user may select "depression" as an input into the patient selection unit 440 in an IMD 200 that was implanted to treat depression. Likewise, other diseases, such as epilepsy, bulimia, traumatic head injury, diabetes, hypertension, etc., may be selected by the user to appropriately communicate and manage the therapy provided by a particular IMD 200.

Based upon this input, the patient management unit 275 executes the appropriate management program/code.

The patient management unit 275 may also comprise a data correlation unit 450. The data correlation unit 450 is capable of correlating various types of data, such as correlating patient parameter data with particular therapy parameter data. Further, data relating to the therapy of a particular patient may be compared or correlated to similar data relating to other patients to provide a user with a context of the type of therapy being delivered. The data correlation unit 450 provides correlated data to be displayed by the GUI interface unit 240. The correlation performed by the data correlation unit 450 may also include providing an indication of the trend of particular correlation of data relating to the responses from therapy. The patient management controller 410 may then provide the resultant data for display as part of a GUI interface unit 240, e.g., a graphical user interface. The patient management controller 410 may also receive data from the GUI interface unit 240 as input from an external user (e.g., a physician input).

FIGS. 5-14 illustrate various screens (e.g., GUI displays) that may be displayed by the GUI interface unit 240 for performing various patient management functions, in accordance with one illustrative embodiment of the present invention. The screen displays in FIGS. 5-14 are exemplary interactive screens, however, those skilled in the art would appreciate that a variety of other screens may be used with the patient management embodiments provided herein and remain within the spirit and scope of the present invention.

FIG. 5 illustrates a GUI screen that provides various information relating to the IMD 200 implanted in a particular patient, wherein the GUI screen may provide for interactive inputs. The screen illustrated in FIG. 5 provides a program patient data "screen" which illustrates various IMD details, such as settings of the patient ID (i.e., a unique identifier, e.g., a code name, initials, code number, etc. designated by a health care provider to identify a patient), the date the device was implanted, the medical condition (indication) for which the patient is being treated with the IMD (i.e., depression), and an identification of the lead model and its serial number. Interactive screens are provided to input data to specify or select each of the foregoing parameters/fields. A virtual keyboard may be provided for this purpose, for use in conjunction with pull-down menus, as shown in the GUI interface of the screen illustrated in FIG. 5. A user, such as the physician, may enter various data using the virtual keyboard and/or pull-down menus. A stylus may also be provided to allow the user to effectively use a small screen, if necessary. The patient management unit 275 (FIG. 2A and FIG. 2B) is capable of receiving this data and displaying the screen provided in FIG. 5.

FIG. 6 illustrates another exemplary screen that may be driven by the patient management unit 275 and displayed by the GUI interface unit 240 (FIG. 2A and FIG. 2B). FIG. 6 illustrates a patient management screen that indicates various electrical signal parameters defining a pulsed therapeutic electrical signal and the power supply capacity of the IMD 200. Interactive inputs/displays provided by the patient management screen of FIG. 6 include indications such as the output current of each pulse, the signal frequency (i.e., number of pulses per second during a signal on-time period), the pulse width, the signal on time, and the signal off time. The IMD 200 may provide an "on-demand" signal triggered by the patient by, for example, a magnet placed over the device. FIG. 6 also illustrates several parameters defining such a "magnet-mode" or on-demand signal, including the "magnet mode" stimulation current, the "magnet mode" on time, and the "magnet mode" pulse width. An indication of whether or not the IMD 200 is "near end of service" may also be provided. This particular screen may be viewed by the user and changes may be made by entering data to set one or more of the parameters listed in FIG. 6. By depressing the "program" button, the displayed parameters in FIG. 6 are entered and applied by the patient management unit 275 to program the IMD 200. Utilizing the screen illustrated in FIG. 6, the electrical signal delivered to the patient by the IMD 200 may be adjusted to modify the therapy in an effort to increase the efficacy of the patient.

Figures 7, 8:
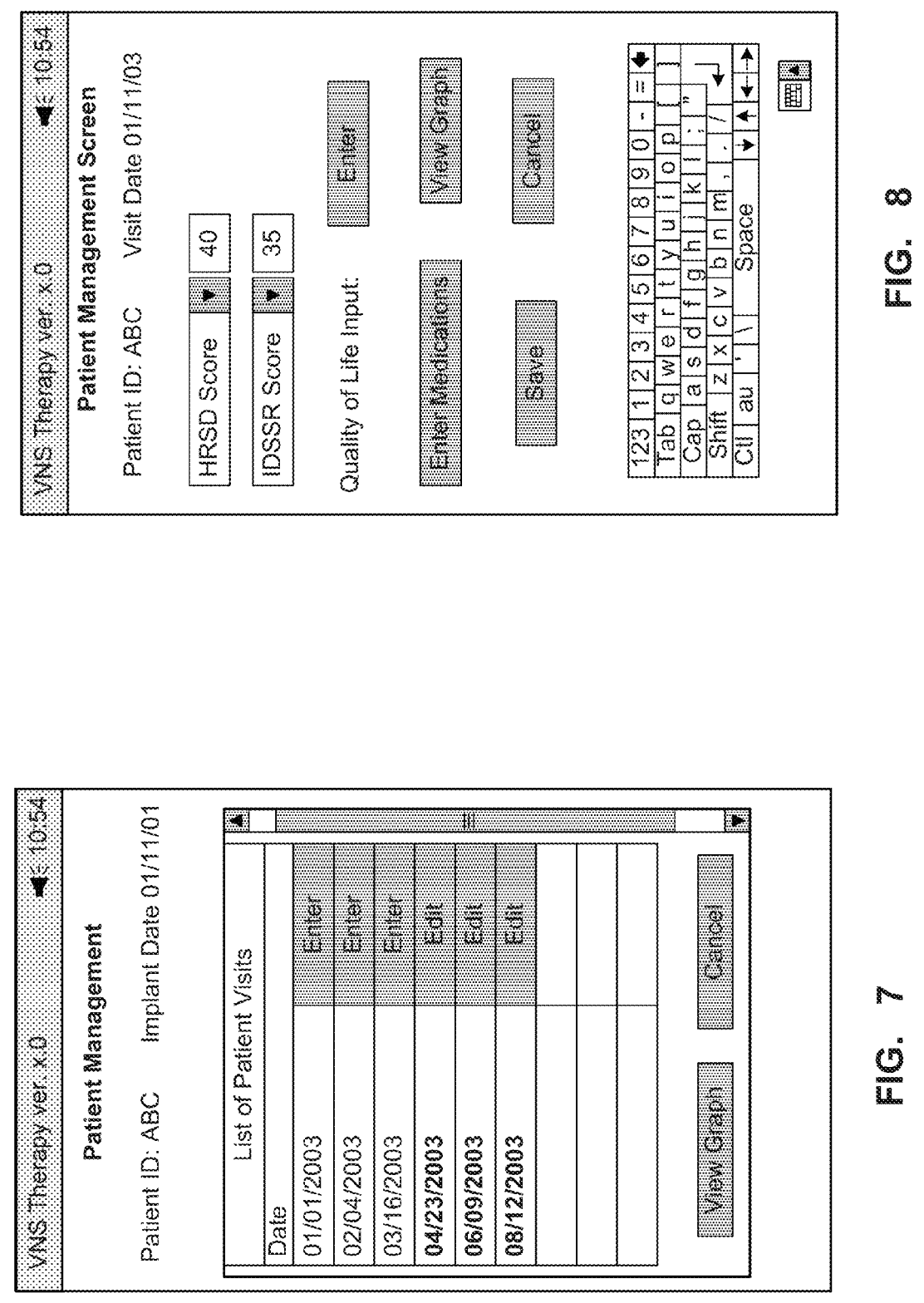

FIG. 7 illustrates a screen driven by the patient management unit 275 and displayed on the GUI interface unit 240 that provides data indicative of a list of patient visits. Patient visits to a physician are logged and remarks may be made as to the details of the visit. Further, a "view graph" input region is provided in this screen to allow a user to select a range of dates and request a corresponding graph, e.g., a graph of a correlation of a particular stimulation parameter to various physiological responses over a three-month period. Changes to the therapy regimen may be made based upon a variety of factors, such as an input from the patient, physical indications observed by the physician in the patient, and other factors that may be input either by the patient and/or a health care provide, such as depression scoring systems and quality of life factors. For example, a number of depression scoring systems may be analyzed by the physician for a particular patient. These scoring systems may be used to track the effectiveness of the therapy being delivered to a patient over the course of time.

FIG. 8 illustrates a screen driven by the patient management unit 275 displayed by the GUI interface unit 240 to allow input of a depression score on one or more depression scoring systems. As illustrated in FIG. 8, data such as the patient ID and the visit dates are displayed along with a particular depression scoring system(s). Examples of depression scoring systems that may be used with embodiments of the present invention include, but are not limited to: the Hamilton Rating Scale for Depression (HRSD), which is a clinician rated scale; the Inventory of Depressive Symptomatology self-report (IDS-SR), which is a patient rated scale; the Inventory of Depressive Symptomatology clinician-administered (IDSSR); the Bech-Rafaelsen Melancholia Scale (MES), which is a clinician rated scale; the Montgomery-Asberg Depression rating Scale (MADRS), which is a clinician rated scale; the Major Depression Inventory (MDI), which is a patient rated scale; the Beck Depression Inventory (BDI), which may be a clinician rated or a patient rated scale; the Hospital Anxiety Depression Scale (HAD), which is a patient rated scale; the Geriatric Depression Scale (GDS); the Clinical Global Impressions Scale (CGI); and the Zung Self Rating Scale for Depression, which is a patient rated scale. The patient management screen of FIG. 8 may be used to enter and analyze other types of depression scoring system and remain within the spirit and scope of the present invention.

An exemplary scoring of the HRSD score and the IDSSR score are displayed in the screen illustrated in FIG. 8. Previous scores and correspondence from particular physician visit dates may be viewed, stored and used in establishing trends of such scores over time for the patient. Further, the current scores may be input using the virtual keypad illustrated in FIG. 8, using pull-down menus as shown. Various other interactive inputs also may be provided, such as the "enter medications" input, which allows a healthcare provided or patient to track medications taken by the patient over time, discussed more fully with reference to FIG. 10 below, and the "view graph" input, which will bring up other correlation screens as described below. These inputs may be facilitated by "virtual buttons" that may be selected by touch-sensitive screen or stylus, e.g. Upon entering the depression scale scores, the patient management unit 275 may perform various calculations to suggest various therapy/stimulation parameter changes for display as prompts to a healthcare provider, who may then implement the suggested modifications and/or make other changes. Alternatively, based on the depression scores, automatic changes to the therapy regimen may be implemented by the patient management unit 275.

Another factor that may be used by the physician or by the patient management unit 275 is a "quality of life" factor. As shown in the screen of FIG. 8 associated with depression rating scales, quality of life measures may also be entered by pressing the "quality of life" input button, which brings up a screen as shown in FIG. 9. The quality of life factors may be used to determine the effectiveness of the therapy regimen. FIG. 9 illustrates another screen driven by the patient management unit and displayed by the GUI interface unit 240 relating to a plurality of quality of life factors. First, one or more of various quality of life rating scales known to those skilled in the art having benefit of the present disclosure may be employed to track the patient's quality of life over time, and to determine one or more parameters in the electrical signal to be implemented by the IMD 200. This is shown in FIG. 9 as a "Quality of Life" pull-down menu, which allows values to be entered for one or more of scales such as, but are not limited to: the generic scale for quality of life; the Psychological General Well-Being Scale (PGWB); the WHO-Five Well-Being Index (WHO-5); the Quality of Life in Depression Scale (QLDS); the Social Functioning Scale-36 (SF-36); the Social Functioning Scale-12 (SF-12); the Quality of Life Enjoyment and Satisfaction Questionnaire-Short Form (Q-LES-Q-SF); and the Streamlined Longitudinal Interval Continuation Evaluation-Condensed Version (SLICE-C). The patient management interface of FIG. 9 may be used to enter, record and analyze other types of quality of life factors and remain within the spirit and scope of the present invention.

As described above, the quality of life factor may be based upon a variety of scales including a generic scale. The generic scale may be selected, as exemplified in FIG. 9. Various scaling numbers associated with the generic scale, such as 1 for very poor, 2 for poor, 3 for average, 4 for good and 5 for excellent may be used. The generic quality of life rating scale may include various factors relating to the patient, such as the alertness of the patient, the verbal skill of the patient, the mood of the patient, the achievements experienced by the patient, the memory level of the patient, an overall quality of life factor from a patient's perspective, as well as a total quality of life score, which may be a mathematical compilation of all of the generic quality of life factors listed above. As an example, the components of the generic quality of life scale are shown as individual pull-down menu items in FIG. 9. It will be appreciated by those with skill in the art having benefit of the present disclosure that other scales such as the PGWB, the WHO-5, the QLDS, etc., may be selected by the physician using the pull-down feature of FIG. 9. Other quality of life fields may be also included but are not illustrated in FIG. 9 for ease of description including, but are not limited to, the energy level of the patient, the performance (e.g., work performance, school performance, etc.) of the patient, the concentration level of the patient, the emotional and mental overview of the patient, the coordination and balance of the patient, the amount of sleep achieved by the patient, and the sexual function levels of the patient.

As indicated in FIG. 9, the generic quality of life factors are displayed and may be entered using the drop down menu screens provided in the interface screen. Based upon the physician's evaluation of the various quality of life functions, the patient management unit 275 may calculate a total quality of life score. The physician may view a graph of one or more of the quality of life factors over time by depressing the "view graph" input provided in the screen of FIG. 9. Further, an "enter medications" input may also be provided in the screen illustrated in FIG. 9, which allows the physician to enter various medications that the patient is taking at a particular time point. Based upon the depression score (FIG. 8) and/or the quality of life inputs provided herein (FIG. 9), an one or more suggested adjustments to the parameters defining the electrical system may be determined by the patient management unit 275 and either displayed for a healthcare provide and/or patient, or automatically implemented by the IMD 200.

In some cases, a patient may be treated for depression by using the electrical signal therapy provided by the IMD 200, as well as by depression-related medications in conjunction with the electrical signal therapy. The patient management unit 275 is capable of keeping track of the medication and the dosage provided to the patient. As noted in the discussion of FIGS. 8 and 9, medications may be entered by pressing the "Enter Medications" button, which leads to a display as shown in FIG. 10. An input screen is provided to allow a healthcare provider or patient to enter various medications currently being prescribed to a patient. Although the interface screen illustrated in FIG. 10 only illustrates four types of medication, those skilled in the art would appreciate that any number of medication inputs and displays may be provided by the patient management unit 275. As an example, medication-1 may be Prozac™ with a 100 mg. dosage and medication-2 may be Effexor™ with a 50 mg. dosage. Other depression-related medications that may be entered into or selected in the interface display of FIG. 10 include, but are not limited to, Adapin™, Anafranil™, Asendin™, Aventyl™, Celexa™ (SSRI), Cymbalta™, Desyrel™, Elavil™, Eskalith™, Lamictal™, Lexapro™ (SSRI), Ludiomil™, Luvox™ (SSRI), Marplan™ (MAOI), Nardil™ (MAOI), Norpramin™, Pamelor™, Parnate™ (MAOI), Paxil™ (MAOI), Pertofrane™, Remeron™, Serzone™, Sinequan™, Surmontin™, Tofranil™, Vestra™, Vivactil™, Wellbutrin™, and Zoloft™ (SSRI).

Various pull-down menus options may be available to enter or select various medications, augmenting agents, and their related dosages, and the frequency of the dosage. A "view graph" input is provided on the interface screen of FIG. 10 to graphically display various factors, such as quality of life versus the type of stimulation delivered (i.e., one or more stimulation parameters defining the electrical signal) and the amount and type of medication provided to the patient. A virtual keyboard is also provided to allow the entry of various medications into the screen provided in FIG. 10, wherein the inputs may then be saved using the "save" input. Alternatively or additionally, pull-down screens using standard medications prescribed for depression may be provided to facilitate rapid indication of the patient's medications. Using the screen of FIG. 10, the physician and/or patient can input and/or examining or display various medications and their related dosages for a particular patient. The inputs provided by the physician may then be stored into the IMD 200 by using commands delivered from the patient management unit 275 to the IMD 200.

Similarly, FIG. 11 illustrates an interface screen similar to that of FIG. 10 that includes various augmenting agents and/or dosages that the patient may have been prescribed. As an example, augmenting agent-1 may be Abilify™ with a 100 mg. dosage and augmenting agent-2 may be Risperdal™ with a 50 mg. dosage. Other depression-related augmenting agents that may be entered into or selected in the interface screen of FIG. 11 include, but are not limited to, Geodon™, Lithobid™, Ritalin™, Strattera™, and Zyprexa™. Various pulldown menus options may be available to enter or select various augmenting agents, related dosage, and the frequency of the dosage. As with the screen of FIG. 10 for medications, a "view graph" input is provided on the interface screen of FIG. 11 to view a graph with various curves, such as quality of life versus the type of stimulation delivered and the amount of augmenting agents provided to the patient. A virtual keyboard is also provided to enter various augmenting agents into the screen provided in FIG. 11. The entered augmenting agents may be saved using the "save" input.

In an alternative embodiment, the depression medications (FIG. 10) and augmenting agents (FIG. 11) may be combined in a single interface screen. The various inputs and medications described above may be used by the physician to record, analyze and/or modify the amount of medication and the therapy delivered to the patient. Alternatively, algorithms provided in the patient management unit 275 may propose or implement automatic changes in one or more electrical signal parameters for delivery of therapy.

The "view graph" button in FIGS. 7-11 may be used to graphically display various factors for analysis of patient progress, such as the depression scores and the quality of life factors. Pressing the "view graph" button causes a screen as shown in FIG. 12 to be displayed. FIG. 12 illustrates an interface screen that provides display options for a user for viewing various correlations of data in a graphical form. For example, graphics option may include a selection of particular depression scores such as the HRDS score and the IDSSR scores, which may then be selected to be viewed with in conjunction with one or more electrical signal parameters, such as the charge delivered during stimulations, which may relate to the output signal amplitude multiplied by the width of the pulse of the signal. Other parameters, such as output current per pulse, signal frequency, pulse width, on-time, off-time, or duty cycle (the ratio of on-time to the sum of on-time and off-time), may additionally or alternatively be used. For example, the depression score, as well as the charge, may be selected, wherein the output current, the signal frequency, the pulse width, and the duty cycle may not be selected as indicated by the "radio button" or "virtual button" selection illustrated in FIG. 12. In one embodiment, the radio or virtual buttons may be used to selectively display certain parameters and avoid others to focus the analysis based upon trends with respect to pre-selected parameters. Similarly, selectable buttons may be provided for selecting the quality of life for graphical display along with various corresponding stimulation parameters, as illustrated in FIG. 12. As an example, after selecting the parameters for display, a user may depress a "launch graph" input to the interface screen. Based upon the selections indicated in FIG. 12 (i.e., the depression score and the corresponding charge per pulse of the electrical signal), depressing the "launch graph" button of FIG. 12 would provide the graphical interface screen illustrated in FIG. 13. The user may graphically display how different parameter adjustment(s) affect the patient's score over a time or view how the charge, for example, affected the scores over time. The ability to display different trends may provide the physician with sufficient information to modify the stimulation to increase efficacy. Further, the user can alternate between the examination of depression scores versus certain examination parameters or quality of life indications versus particular stimulation parameters.

Figure 13:
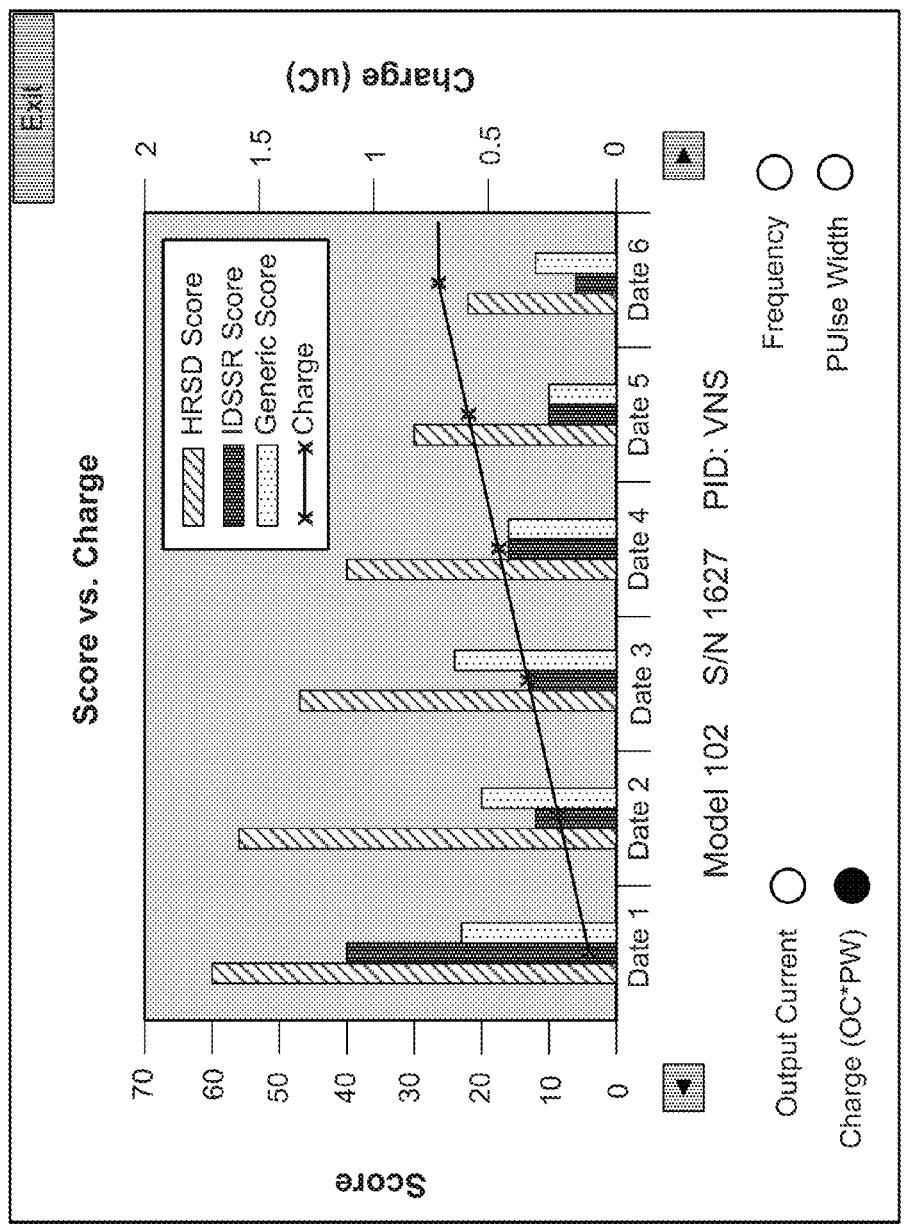
FIG. 13 illustrates an exemplified graphical depiction of the depression scores HRSD and IDSSR, and a generic "quality of life" score correlated with the corresponding charge of the stimulation signal over time, according to some embodiments of the present disclosure.

FIG. 13 illustrates an exemplified graphical depiction of the depression scores HRSD and IDSSR, and a generic "quality of life" score correlated with the corresponding charge of the stimulation signal over time. More specifically, the graphical representation of FIG. 13 illustrates a series of time periods and corresponds to particular depression scores, the generic quality of life score and also the corresponding charge of the stimulation signal. The exemplary interface screen illustrated in FIG. 13 shows that a relative decline in the depression score is found over time as the charge of the stimulation signal rises. The interface screen of FIG. 13 also allows for modification of the graphical representation by depressing one or more "virtual buttons" that may be used to select the output current, the frequency and/or the pulse width as well as the charge for trend display. The physician accessing the information provided in the interface screen of FIG. 13 may use this data to determine if a patient's current settings are effective in lowering depression scores. The physician has the option of charting different parameters versus the depression scores. Using the display of FIG. 13, the physician may decide to modify the medication and/or the therapy delivered to the patient.

Figure 14:
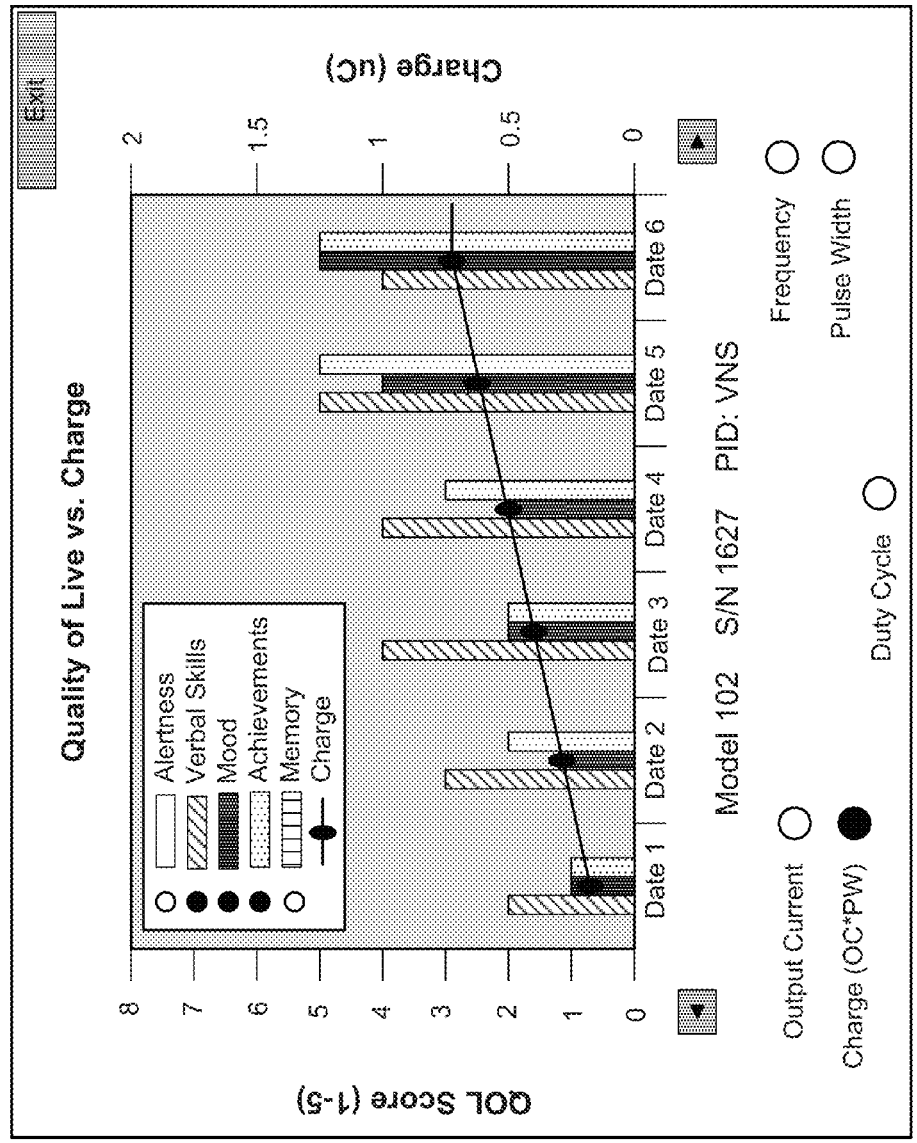
FIG. 14 illustrates a quality of life display in relation to particular stimulation parameters, according to some embodiments of the present disclosure.

FIG. 14 illustrates a quality of life display in relation to particular stimulation parameters. For example, the user may select particular quality of life factors, such as the verbal skills, mood factors, achievement factors, and display these factors in conjunction with the charge of the stimulation signal delivered or other electrical signal parameters. The example of FIG. 14 illustrates that the various quality of life indications, which may be selected using the "virtual buttons" shown in the figure, have improved for the patient in relative proportion to the increase in the charge of the stimulation signal delivered by the IMD 200. Using this or similar information, the physician may be able to evaluate whether the patient's current settings are effective, which may lead to adjustment that may result in an improvement of one or more aspects of the patient's quality of life. Various other types of quality of life factors may also be analyzed by embodiments of the present invention and remain within the scope and spirit of the present invention. In addition to the interface screens shown in FIGS. 5-14, those skilled in the art having benefit of the present disclosure may implement various other interface screens for interactive communication using GUI interface unit 240.

Figure 15:
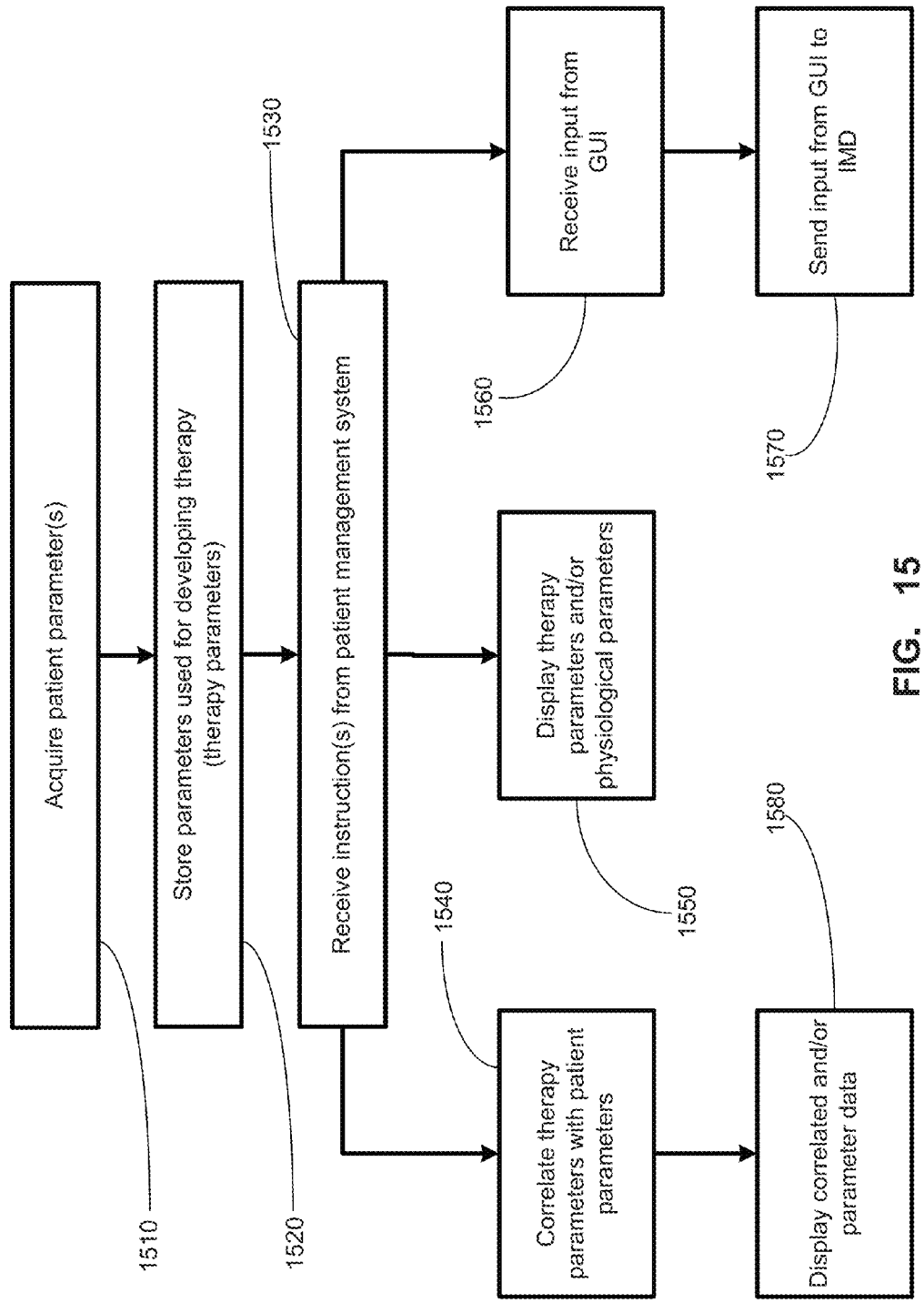
FIG. 15 is a flowchart of a method of performing the patient management function in accordance with one illustrative embodiment of the present invention.

Turning now to FIG. 15, a flowchart depiction associated with the methods of performing the patient management function of the present invention is illustrated. In order to maintain proper operation of the patient management unit 275, the IMD 200 may be prompted to periodically acquire patient parameters associated with various portions of the patient's body (block 1510). Acquisition of patient parameters may include various physical indications, quality of life indications, depression scores, etc. The IMD 200 may also store the various stimulation parameters used for delivering the therapy (block 1520).

A portion of the external unit 270 may receive instructions from the patient management unit 275 to perform various tasks (block 1530). Based upon the instructions received, the external unit 270 may correlate therapy parameters with patient parameters (block 1540). Alternatively, this task may also be performed by the IMD 200. The correlation of therapy parameters provides for associating particular therapy parameters with certain physiological indications and/or quality of life indications at certain time periods. For example, a 24-hour period after the delivery of a particular regimen of stimulation signals may be used as a time period for acquiring various patient data. Alternatively, every physician visit may be used as a benchmark for logging quality of life parameters, which may be input into the GUI interface unit 240 by the physician. The correlated data and/or a list of patient parameters or therapy parameter data may be displayed onto the GUI interface unit 240 (block 1550).

The patient management system may also provide for displaying the therapy parameters and/or patient parameters based upon the instructions received (block 1550). Several parameters, such as the depression scores, may be displayed along with one or more therapeutic electrical signal parameters. Therefore, the physician may examine various displays indicative of the patient's general health trends and the efficacy of the effectiveness of the therapy being delivered and modify the operation of the IMD 200 to prove patient efficacy. More automated logging, organizing, displaying of IMD data, and controlling the operation of the IMD 200 may be performed using the patient management system provided by embodiments of the present invention.

Many advantages may be realized by utilizing the patient management tool provided by embodiments of the present invention. The patient management tool provided herein may be incorporated into the VNS Therapy™ Programming Software. One advantage of utilizing the patient management tool of the present invention is presenting a physician with a software tool that is not time consuming when documenting parameters and patient information. Another advantage of utilizing the patient management tool of the present invention is that the physician would be able to quickly view the progress of the patient receiving therapy from an IMD 200 by graphing the information stored in the database unit 250 and or the local database unit 255. The graphs may be printed and placed in the patient's chart and may also be available to the patient. As time progresses the collection of data on all the patients may be statistically analyzed to determine which settings appear to be efficacious for most patients. Additionally, this information may be stored in a database and can easily be downloaded on a physician's computing device (e.g., desktop computer, lap-top computer, network computer/terminal, hand-held computing device, etc.) for further evaluation.

All of the methods and apparatuses disclosed and claimed herein may be made and executed without undue experimentation in light of the present disclosure. While the methods and apparatus of this invention have been described in terms of particular embodiments, it will be apparent to those skilled in the art that variations may be applied to the methods and apparatus and in the steps or in the sequence of steps of the method described herein without departing from the concept, spirit, and scope of the invention, as defined by the appended claims. It should be especially apparent that the principles of the invention may be applied to selected cranial nerves other than the vagus nerve to achieve particular results.

The particular embodiments disclosed above are illustrative only as the invention may be modified and practiced in different but equivalent manners apparent to those skilled in the art having the benefit of the teachings herein. Furthermore, no limitations are intended to the details of construction or design herein shown other than as described in the claims below. It is, therefore, evident that the particular embodiments disclosed above may be altered or modified and all such variations are considered within the scope and spirit of the invention. Accordingly, the protection sought herein is as set forth in the claims below.

What is claimed:

1. A method comprising:
   acquiring, at a patient management unit, therapy parameter data relating to an electrical signal provided by an implantable medical device to a cranial nerve of a particular patient;
   generating, at the patient management unit, data representing a depression therapy regimen provided to the particular patient, wherein the data further represents a relationship between the therapy parameter data and second therapy parameter data associated with one or more other patients, wherein the particular patient is distinct from the one or more other patients;
   displaying, at a display device of the patient management unit, a graphical representation that depicts the data representing the depression therapy regimen;
   displaying, at the display device, adjustment information indicating one or more suggested adjustments to one or more parameters of the electrical signal for providing the depression therapy regimen, wherein the one or more suggested adjustments are determined based on a depression score and a quality of life parameter; and
   modifying, at the patient management unit, the depression therapy regimen based at least in part on the relationship between the therapy parameter data and the second therapy parameter data.

2. The method of claim 1, further comprising:
   receiving, at the patient management unit, at least a portion of physician evaluation data from a healthcare provider; and
   determining, at the patient management unit, a second relationship between the therapy parameter data and the portion of the physician evaluation data.

3. The method of claim 2, wherein the physician evaluation data is based at least in part on an evaluation from the healthcare provider associated with the particular patient, and wherein the evaluation is based on a patient alertness parameter, a patient verbal skills parameter, a patient mood parameter, a patient achievement parameter, a patient memory parameter, an energy level parameter, a performance parameter, a concentration level parameter, an emotional parameter, a mental overview parameter, a coordination parameter, a balance parameter, an amount of sleep parameter, a sexual function level parameter, or a combination thereof.

4. The method of claim 2,
   wherein the graphical representation further depicts one or more first trends related to a magnitude of the physician evaluation data and one or more second trends related to a magnitude of at least one of a plurality of user selected therapy parameters;
   wherein the plurality of user selected therapy parameters comprises at least one of a plurality of electrical signal parameters, at least one of a plurality of medication parameters, or both;
   wherein the plurality of electrical signal parameters comprises a current amplitude, a voltage amplitude, a rate of change of the current amplitude, a time period of the rate of change of the current amplitude, a rate of change of the voltage amplitude, a time period of the rate of change of the voltage amplitude, a pulse width, a rate of change of the pulse width, a time period of the rate of change of the pulse width, a frequency, a rate of change of the frequency, a time period of the rate of change of the frequency, a signal on time, a signal off time, or a combination thereof; and wherein the plurality of medication parameters comprises a name of a medication, a dosage of the medication, or a combination thereof.

5. The method of claim 2, further comprising providing an interface that enables modification of the graphical representation to further depict data corresponding to one or more parameters of the therapy parameter data, one or more parameters of the physician evaluation data, or both.

6. The method of claim 5, wherein the interface comprises a graphical user interface for receiving a value of at least one therapy parameter, wherein the at least one therapy parameter is associated with a medication, a dosage associated with the medication, or both.

7. The method of claim 2, wherein the graphical representation further depicts:
  values of the physician evaluation data corresponding to a plurality of time intervals; and
  values of the therapy parameter data corresponding to the plurality of time intervals.

8. The method of claim 2, wherein the physician evaluation data is related to a condition of the particular patient and wherein the physician evaluation data comprises a side effect parameter including a breathing rate, a heart rate, or both.

9. The method of claim 8, wherein the side effect parameter is sensed by the implantable medical device.

10. The method of claim 1, wherein the graphical representation further depicts sensed body parameter data, wherein the sensed body parameter data comprises a value sensed by the implantable medical device from a tissue of the particular patient, and wherein the depression therapy regimen is further modified based at least in part on the sensed body parameter data.

11. The method of claim 10, wherein the implantable medical device uses the sensed body parameter as feedback to modify the electrical signal provided to the cranial nerve of the particular patient within stimulation parameters that correspond to the depression therapy regimen.

12. The method of claim 1, wherein the therapy parameter data comprises an indication of a current amplitude, a voltage amplitude, a rate of change of the current amplitude, a time period of the rate of change of the current amplitude, a rate of change of the voltage amplitude, a time period of the rate of change of the voltage amplitude, a pulse width, a rate of change of the pulse width, a time period of the rate of change of the pulse width, a frequency, a rate of change of the frequency, a time period of the rate of change of the frequency, a signal on time, a signal off time, or a combination thereof.

13. The method of claim 1, wherein the implantable medical device provides passive stimulation to the cranial nerve of the particular patient within stimulation parameters that correspond to the depression therapy regimen.

14. The method of claim 1, wherein the graphical representation further depicts one or more trends, wherein the one or more trends comprise one or more scores over a plurality of time intervals, and wherein each of the one or more scores comprise a value sensed by the implantable medical device.

15. The method of claim 14, wherein the one or more scores comprise the depression score.

16. The method of claim 14, wherein the one or more scores comprise the quality of life parameter.

17. The method of claim 14, further comprising receiving a selection of the one or more trends and the one or more scores to be depicted by the graphical representation.

18. A computer readable program storage device encoded with instructions that, when executed by a processor, cause the processor to:
  acquire, at a patient management unit, therapy parameter data relating to an electrical signal provided by an implantable medical device to a cranial nerve of a particular patient;
  generate, at the patient management unit, data representing a depression therapy regimen provided to the particular patient, wherein the data further represents a relationship between the therapy parameter data and second therapy parameter data associated with one or more other patients, wherein the particular patient is distinct from the one or more other patients;
  display, at a display device of the patient management unit, a graphical representation that depicts the data representing the depression therapy regimen;
  display, at the display device, adjustment information indicating one or more suggested adjustments to one or more parameters of the electrical signal for providing the depression therapy regimen, wherein the one or more suggested adjustments are determined based on a depression score and a quality of life parameter; and
  modify, at the patient management unit, the depression therapy regimen based at least in part on the relationship between the therapy parameter data and the second therapy parameter data.

19. The computer readable program storage device of claim 18, wherein the instructions are further executable by the processor to receive, at the patient management unit, at least a portion of physician evaluation data from a healthcare provider.

20. The computer readable program storage device of claim 19, wherein the graphical representation further depicts a second relationship of historical values of a first parameter of the physician evaluation data, a third relationship of historical values of a second parameter of the physician evaluation data, and a trend of historical values corresponding to the therapy parameter data.

21. The computer readable program storage device of claim 20, wherein the instructions are further executable by the processor to receive input associated with a third parameter of the physician evaluation data, wherein the third parameter is distinct from the first parameter and is distinct from the second parameter, wherein the graphical representation is modified responsive to the input to display a fourth relationship between historical values of the third parameter of the physician evaluation data and the historical values corresponding to the therapy parameter data.

* * * * *